United States Patent [19]

Hilverda

[11] Patent Number: Plant 7,113

[45] Date of Patent: Jan. 16, 1990

[54] CARNATION NAMED HILSWISS

[75] Inventor: Jan J. Hilverda, Aalsmeer, Netherlands

[73] Assignee: Hilverda b.v., Aalsmeer, Netherlands

[21] Appl. No.: 308,757

[22] Filed: Feb. 10, 1989

[51] Int. Cl.[4] ..... A01H 5/00

[52] U.S. Cl. ..... Plt./70

[58] Field of Search ..... Plt./70

*Primary Examiner*—Robert E. Bagwill

*Attorney, Agent, or Firm*—Charles W. Rummler

[57] ABSTRACT

A new spray carnation variety particularly distinguished by its continuous and profuse production of relatively small flowers having basically white petals characterized by currrant red picotee at the petal margins and a few marginal stripes of the same color which cause the bloom to have a very attractive rosy appearance, the blooms being borne on erect, rigid stems of about 60 cm. in length, there being more than three flowers per stem. The plant has a strong, vigorous and upright growth habit with abundant foliage, a rapid growth habit and a total height of approximately 100 cm.

1 Drawing Sheet

BACKGROUND OF THE NEW PLANT

This new spray carnation cultivar originated as a seedling of a hybrid resulting from my crossing of two unnamed and unpatented carnation varieties selected from my collection of carnation plants maintained by me for breeding purposes at my nursery in Aalsmeer, The Netherlands, the object of this crossing being to improve the range of varieties for commercial production of plants having more rapid growth, better flower colors and improved production rate. This particular seedling was selected by me for propagation because of the almost pure white general coloration of its flower petals characterized by red picotee at all petal margins and occasional inwardly-extending red marginal stripes and propagation was done by me at Aalsmeer by means of cuttings with such satisfactory results that this new carnation variety was propagated under my direction at Aalsmeer for several successive generations by means of cuttings, which clearly demonstrated that the new plant would maintain its distinctive characteristics from generation to generation and that its homogenetic character could be assured for commercial production.

DESCRIPTION OF THE DRAWING

My new spray carnation variety is illustrated by the accompanying photographic drawing which shows, in full color, a flower stem having blooms and buds in several stages of maturity, as well as a face view of the flower, several petals and a bud at the beginning of its opening stage, the colors shown being as nearly true as is reasonably possible to obtain by conventional photographic procedures.

DESCRIPTION OF THE NEW PLANT

The following is a detailed description of my new spray carnation cultivar based upon observations made during the current year at Aalsmeer, the color designations being according to The R.H.S. Colour Chart published by The Royal Horticultural Society of London, England.

THE PLANT

Origin: Seedling.

Parentage:

*Seed parent.*—An unnamed and unpatented variety.

*Pollen parent.*—An unnamed and unpatented variety. Both varieties having been selected by me from my collection of carnation varieties maintained at Aalsmeer for breeding purposes.

Classification:

*Botanic.*—*Dianthus caryophyllus* L.

*Commercial.*—Spray Carnation.

Form: An erect and tall bush with several stems emitted near the ground.

Growth: Rapid, vigorous, upright and strong.

Height: Approximately 100 cm.

Branching character: Alternate.

Foliage:

*Quantity.*—Abundant.

*Leaf size.*—Averages about 12 to 14 cm. in length.

*Leaf shape.*—Elliptic with entire margins.

*Texture.*—Leathery.

*Color.*—Upper side, Blue Green. Under side, Blue Green.

*Leaflets.*—None.

*Ribs and veins.*—The midrib is prominent.

THE BUD

Size: Medium.

*Diameter.*—About 25 to 30 mm.

*Length.*—About 23 mm.

Form: Cylindrical.

Opening Rate: With a mature bud, the flower petals show in about five days.

Color of petals: When sepals first divide: White and Red. When petals begin to unfurl: White with Red picotee and Red marginal stripes.

Sepals:

*Number.*—Five or six.

*Size.*—Average.

*Shape.*—Generally ovate with an acute tip.

*Character.*—The sepals are hooded over the bud before dividing and stand up as the flower petals unfurl.

*Color.*—Inside: Light green. Outside: Dark green.

*Striae.*—A few, small light green stripes.

Calyx:

*Shape.*—Cylindrical.
*Size.*—Medium.
*Splitting.*—The calyx does not split.
*Aspect.*—Smooth.

Flower stem:
*Length.*—Approximately 60 mm., in average.
*Character.*—Rigid and erect.
*Color.*—Dark green.

THE FLOWER

Blooming habit: Continuous with profuse flower production.

Size of bloom: Small.
*Diameter.*—About 45 to 50 mm.
*Depth.*—Approximately 25 mm.

Borne: In clusters on straight stems emitted in longitudinally-spaced relation from a tall, strong and erect main stem.

Flower shape:
*When bloom first opens.*—High-centered.
*When bloom matures.*—Tends to flatten.

Petalage:
*Number of petals.*—In average, about 52 to 54.
*Arrangement.*—Imbricated.
*Form.*—Fan-shaped with dentated margins and a generally rounded outer end.
*Texture.*—Soft.
*Aspect.*—Velvety.
*Color.*—All petals are substantially the same color with a generally White body, RHS 155-D, with Currant Red picotee, RHS 47-A, and marginal stripes.

Discoloration after full bloom: None.

Fragrance: Weak.

Persistence: The flowers hang on and dry.

Lasting quality: As a cut flower, ten to fourteen days.

REPRODUCTIVE ORGANS

Stamens:
*Number.*—Five to six.
*Arrangement.*—Evenly around the ovary.
*Anthers.*—Size: Normal. Color: Cream white.
*Filaments.*—Length: Approximately 30 mm. Color: White.
*Pollen.*—Color: White.

Pistils:
*Number.*—One.
*Style.*—Length: Approximately 30 mm. Color: White.
*Stigma.*—Color: White.

Character of ovaries: Normal.

THE FRUIT

Fertility: The fruit is fertile.

Shape: Lozenge-shaped.

Color at maturity: Wellow/brown.

This spray carnation most nearly resembles the variety 'Fashion' (unpatented). The new variety is distinguished from 'Fashion', however, because the base color of the petals is white instead of cream yellow, the foliage color is somewhat greener and the plant has a more rapid growth rate.

I claim:

1. The new and distinct spray carnation variety, substantially as herein shown and described, characterized by its relatively small flowers having basically white petals, red picotee along its marginal edges and red marginal stripes, its continuous and profuse blooming habit with the flowers carried on a long flower stem, and its vigorous and upright growth habit with abundant foliage.

* * * * *

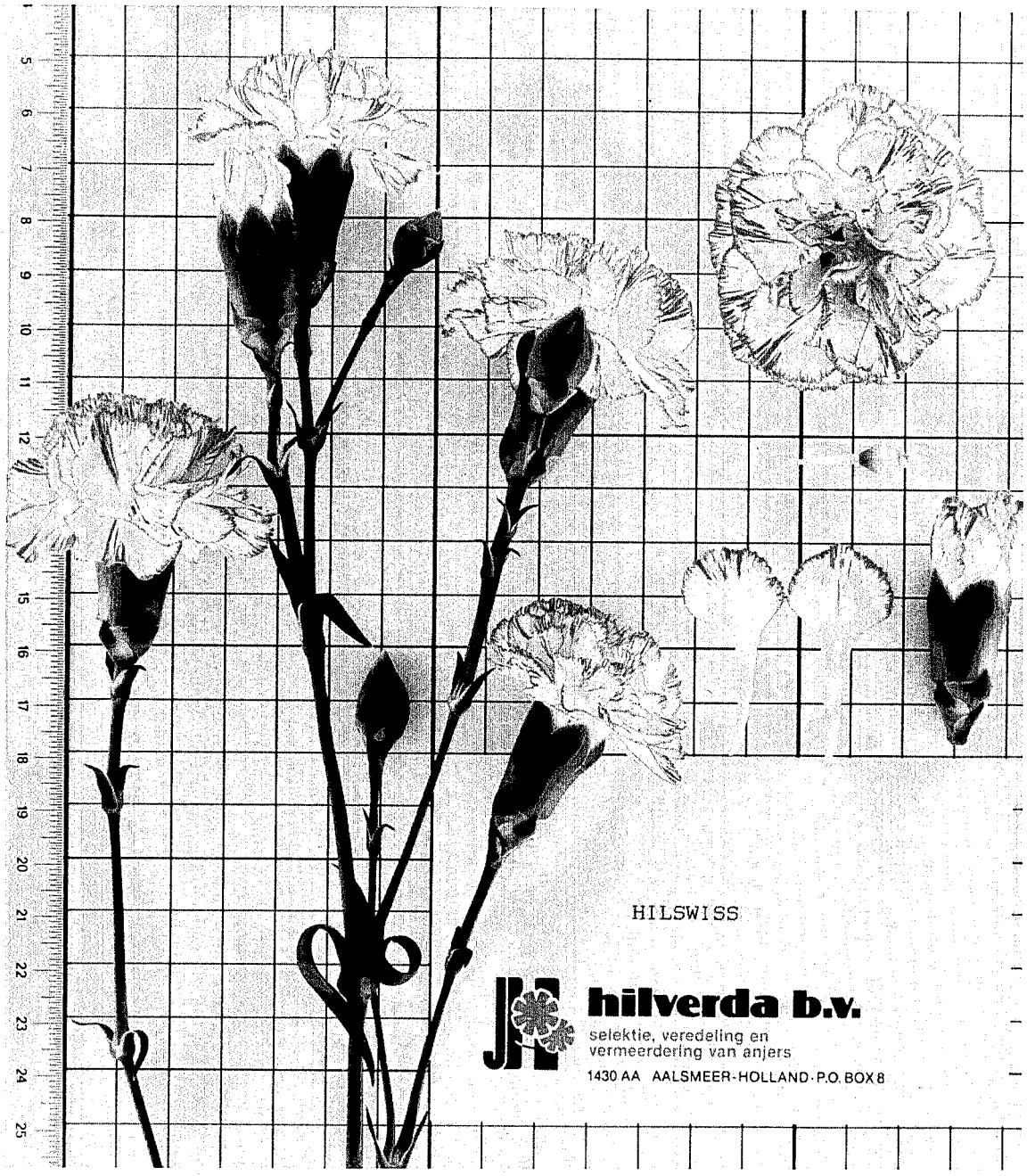
HILSWISS
hilverda b.v.
selektie, veredeling en
vermeerdering van anjers
1430 AA AALSMEER-HOLLAND · P.O. BOX 8